(12) United States Patent
Toscano et al.

(10) Patent No.: US 11,926,580 B2
(45) Date of Patent: Mar. 12, 2024

(54) HYDROPERSULFIDE PRECURSORS

(71) Applicant: THE JOHNS HOPKINS UNIVERSITY, Baltimore, MD (US)

(72) Inventors: John Pasquale Toscano, Baltimore, MD (US); Vinayak S. Khodade, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 17/268,616

(22) PCT Filed: Aug. 30, 2019

(86) PCT No.: PCT/US2019/048969
§ 371 (c)(1),
(2) Date: Feb. 16, 2021

(87) PCT Pub. No.: WO2020/047359
PCT Pub. Date: Mar. 5, 2020

(65) Prior Publication Data
US 2021/0179553 A1  Jun. 17, 2021

Related U.S. Application Data

(60) Provisional application No. 62/725,549, filed on Aug. 31, 2018.

(51) Int. Cl.
*C07C 335/30* (2006.01)
(52) U.S. Cl.
CPC .................. *C07C 335/30* (2013.01)

(58) Field of Classification Search
None
See application file for complete search history.

(56) References Cited

U.S. PATENT DOCUMENTS 4,293,691 A   10/1981   Furutachi et al.

OTHER PUBLICATIONS

Zhao et al. (Bioorganic & Medicinal Chemistry Letters, 2016, 26(18), 4414). (Year: 2016).*
Mustafa AK, Gadalla MM, Snyder SH. Signaling by gasotransmitters. Sci Signal. Apr. 28, 2009;2(68):re2. doi: 10.1126/scisignal. 268re2. PMID: 19401594; PMCID: PMC2744355.

(Continued)

*Primary Examiner* — Sudhakar Katakam
*Assistant Examiner* — Jennifer C Sawyer
(74) *Attorney, Agent, or Firm* — Casimir Jones, SC; Jeffrey W. Childers

(57) ABSTRACT

A hydropersulfide precursor compound having the formula (I): formula (I) as defined in the specification. A process for preparing the hydropersulfide precursor, and a method of using the precursor to generate hydropersulfide are also described.

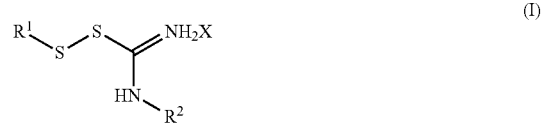

17 Claims, 3 Drawing Sheets

| | $R^1$ | $R^2$ | | $R^1$ | $R^2$ |
|---|---|---|---|---|---|
| 4a | H | H | 4e | H | 4-MeOPh |
| 4b | H | $CH_3$ | 4f | H | 2-ClPh |
| 4c | $CH_3$ | H | 4g | H | 4-ClPh |
| 4d | H | Ph | 4h | H | 4-$CF_3$Ph |

(56) References Cited

OTHER PUBLICATIONS

Ida T, Sawa T, Ihara H, Tsuchiya Y, Watanabe Y, Kumagai Y, Suematsu M, Motohashi H, Fujii S, Matsunaga T, Yamamoto M, Ono K, Devarie-Baez NO, Xian M, Fukuto JM, Akaike T. Reactive cysteine persulfides and S-polythiolation regulate oxidative stress and redox signaling. Proc Natl Acad Sci U S A. May 27, 2014;111(21):7606-11. doi: 10.1073/pnas.1321232111. Epub Apr. 14, 2014. PMID: 24733942; PMCID: PMC4040604.

Chauvin Jr, Griesser M, Pratt DA. Hydropersulfides: H-Atom Transfer Agents Par Excellence. J Am Chem Soc. May 10, 2017;139(18):6484-6493. doi: 10.1021/jacs.7b02571. Epub Apr. 28, 2017. PMID: 28419803.

Bailey TS, Pluth MD. Reactions of isolated persulfides provide insights into the interplay between H2S and persulfide reactivity. Free Radic Biol Med. Dec. 2015;89:662-7. doi: 10.1016/j.freeradbiomed. 2015.08.017. Epub Oct. 8, 2015. PMID: 26454077; PMCID: PMC4684792.

Cuevastana E, Lange M, Bonanata J, Coitiño EL, Ferrer-Sueta G, Filipovic MR, Alvarez B. Reaction of Hydrogen Sulfide with Disulfide and Sulfenic Acid to Form the Strongly Nucleophilic Persulfide. J Biol Chem. Nov. 6, 2015;290(45):26866-26880. doi: 10.1074/jbc.M115.672816. Epub Aug. 12, 2015. PMID: 26269587; PMCID: PMC4646399.

Artaud I, Galardon E. A persulfide analogue of the nitrosothiol SNAP: formation, characterization and reactivity. Chembiochem. Nov. 3, 2014;15(16):2361-4. doi: 10.1002/cbic.201402312. Epub Sep. 9, 2014. PMID: 25205314.

Tsurugi, Jitsuo, Sunichi Kawamura, and Toyokazu Horii. "Aryl hydrodisulfides." The Journal of Organic Chemistry 36.24 (1971): 3677-3680.

Zheng Y, Yu B, Li Z, Yuan Z, Organ CL, Trivedi RK, Wang S, Lefer DJ, Wang B. An Esterase-Sensitive Prodrug Approach for Controllable Delivery of Persulfide Species. Angew Chem Int Ed Engl. Sep. 18, 2017;56(39):11749-11753. doi: 10.1002/anie.201704117. Epub Aug. 16, 2017. PMID: 28700817.

Powell CR, Dillon KM, Wang Y, Carrazzone RJ, Matson JB. A Persulfide Donor Responsive to Reactive Oxygen Species: Insights into Reactivity and Therapeutic Potential. Angew Chem Int Ed Engl. May 22, 2018;57(21):6324-6328. doi: 10.1002/anie. 201803087. Epub Apr. 26, 2018. PMID: 29697170; PMCID: PMC6159213.

Cossar, B. C., et al. "Preparation of thiols." The Journal of organic chemistry 27.1 (1962): 93-95.

Rad, MN Soltani, and Saeid Maghsoudi. "Two-step three-component process for one-pot synthesis of 8-alkylmercaptocaffeine derivatives." RSC advances 6.74 (2016): 70335-70342.

Wang, Xue-Feng, et al. "Synthesis and biological evaluation of disulfides bearing 1, 2, 4-triazole moiety as antiproliferative agents." Medicinal Chemistry Research 26.12 (2017): 3367-3374.

Stellenboom, Nashia, Roger Hunter, and Mino R. Caira. "One-pot synthesis of unsymmetrical disulfides using 1-chlorobenzotriazole as oxidant: Interception of the sulfenyl chloride intermediate." Tetrahedron 66.17 (2010): 3228-3241.

Khodade, Vinayak S., and John P. Toscano. "Development of S-substituted thioisothioureas as efficient hydropersulfide precursors." Journal of the American Chemical Society 140.50 (2018): 17333-17337.

PCT International Search Report and Written Opinion for corresponding International Application Serial No. PCT/US2019/048969, dated Aug. 30, 2019, pp. 1-6.

* cited by examiner

HYDROPERSULFIDE PRECURSORS

RELATED APPLICATIONS

This application claims the benefit of U.S. Provisional Patent Application Ser. No. 62/725,549, filed Aug. 31, 2018, the entirety of which is hereby incorporated by reference for all purposes.

GOVERNMENT FUNDING

This invention was made with government support under grant number CHE-1566065 awarded by the National Science Foundation. The Government has certain rights in the invention.

BACKGROUND

Hydrogen sulfide ($H_2S$) is a biologically important signaling molecule that exerts diverse roles in a myriad of physiological processes. However, recent reports indicate that much of $H_2S$ biological activity may be attributed to hydropersulfides (RSSH) and/or polysulfides ($RSS_nR$). Mustafa et al., Sci. Signal. 2, 72 (2009). RSSH have been detected in tissues, cells, and plasma at submicromolar to micromolar concentrations and play a regulatory role in redox biology. Ida et al., Proc. Natl. Acad. Sci. U.S.A., 111, 7606-7611 (2014). For example, persulfidation of Keap-1 releases Nrf-2, which induces the expression of anti-inflammation genes. RSSH are also excellent hydrogen transfer agents towards a variety of radicals. Chauvin et al., J. Am. Chem. Soc., 139, 6484-6493 (2017). Despite increasing evidence of the role of RSSH in redox signaling, the fundamental chemistry and biological roles of RSSH are still poorly understood. This deficiency is partly due to the unstable nature of RSSH in aqueous solution where, in the absence of traps, conversion to trisulfides, tetrasulfides, elemental sulfur, and $H_2S$ is observed. Bailey, T. S.; Pluth, M. D., Free Radic. Biol. Med., 89, 662-667 (2015). Because of this reactivity, RSSH are typically generated in situ.

Several methods have been reported to produce RSSH. For example, reaction of sulfide salts ($Na_2S$ or NaSH) with disulfides generates RSSH (Scheme 1, eq. 1). Cuevasanta, J. Biol. Chem., 290, 26866-26880 (2015). However, because disulfide, $H_2S$, RSSH, and thiol, are in equilibrium, the effects of RSSH are difficult to evaluate exclusively. Several approaches to generate RSSH in a controllable fashion have also been reported. RSSH can be produced via acid-mediated hydrolysis of acyl disulfides (Scheme 1, eq. 2 (Tsurugi et al., J. Org. Chem., 36, 3677-3680 (1971))), although hydrolysis appears to be slow ($t_{1/2}$>12 h) making RSSH study difficult. In another approach, a precursor containing an activated disulfide bond has been developed in which a methoxycarbonyl group transfer from sulfur to nitrogen under physiological conditions produces RSSH (Scheme 1, eq. 3). Isabelle, A.; Erwan, G., ChemBioChem, 15, 2361-2364 (2014). Recently, Wang and co-workers developed RSSH precursors that can be activated by esterase to produce RSSH (Scheme 1, eq. 4). Zheng et al., Angew. Chem., Int. Ed., 56, 11749-11753 (2017) Similarly, Xian and co-workers reported O-silyl-mercaptan-based RSSH precursors which undergo pH- or fluoride-mediated desilylation to release RSSH in a controlled fashion (Scheme 1, eq. 5). In addition, Matson and co-workers have developed a hydrogen peroxide activated RSSH donor. Powell et al., Angew. Chem., Int. Ed., 57, 6324-6328 (2018).

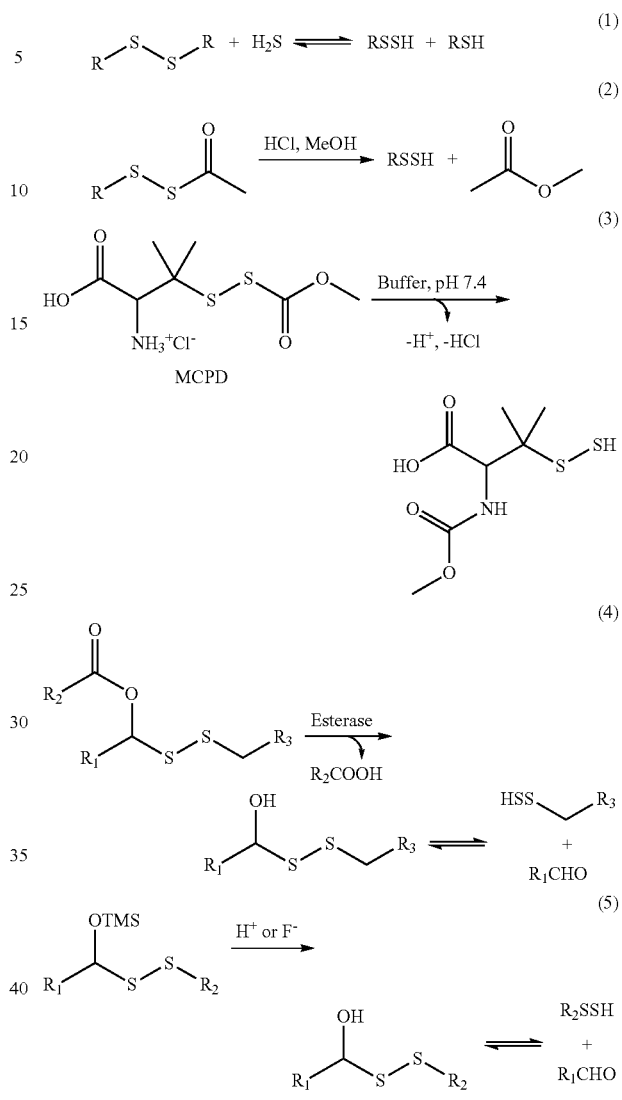

To advance our understanding of RSSH roles in biology, the development of new precursors that can cleanly and reliably produce RSSH under biological conditions is critical.

SUMMARY

Due to their inherent instability, hydropersulfides (RSSH) must be generated in situ using precursors, but very few physiologically useful RSSH precursors have been developed to date. The design, synthesis, and evaluation of novel S-substituted thiosiothioureas as RSSH precursors is described herein. These water-soluble precursors show efficient and controllable release of RSSH under physiological conditions.

BRIEF DESCRIPTION OF THE FIGURES

The present disclosure may be more readily understood by reference to the following drawings, wherein.

DETAILED DESCRIPTION

Figure 1:
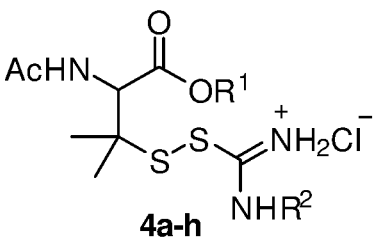
FIG. 1 provides the chemical structures of hydropersulfide precursors 4a-h.

The present disclosure provides a hydropersulfide precursor compound having the formula (I):

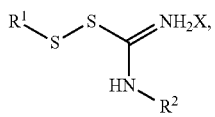
(I)

wherein $R^1$ is a $C_1$-$C_6$ alkyl group optionally substituted with one or more of a carboxylic acid, C(O)OR$^a$, NHC(O)R$^b$, NHC(O)(CH$_2$)$_2$CH(NHC(O)R$^c$)(COOR$^d$), NHC(O)(CH$_2$)$_2$CH(NH$_2$)(COOR$^d$), C(O)NHCH$_2$COOR$^e$, and a phenyl group optionally substituted with a lower alkyl, lower alkoxy, or trifluoromethyl moiety;
$R^2$ is H, a $C_1$-$C_6$ alkyl moiety, or a $C_6$-$C_{10}$ aryl group that is optionally substituted with a halogen, lower alkyl, lower alkoxy, or trifluoromethyl moiety;
X is a halogen; and wherein
R$^a$ is a $C_1$-$C_{20}$ alkyl moiety or a peptide chain comprising of 1-5 amino acids;
R$^b$ is a $C_1$-$C_{20}$ alkyl moiety;
R$^c$ is a $C_1$-$C_{20}$ alkyl moiety;
R$^d$ is H, a $C_1$-$C_{20}$ alkyl moiety, or a peptide chain comprising of 1-5 amino acids; and
R$^e$ is H or a $C_1$-$C_{20}$ alkyl moiety.

A process for preparing the hydropersulfide precursor, and a method of using the precursor to generate hydropersulfide are also described.

Definitions

The terminology as set forth herein is for description of the embodiments only and should not be construed as limiting of the disclosure as a whole. As used herein, the singular forms "a", "an", and "the" are inclusive of their plural forms, unless contraindicated by the context surrounding such.

As used herein, the term "about" refers to +/−10% deviation from the basic value.

As used herein, the term "organic group" is used to mean a hydrocarbon group that is classified as an aliphatic group, cyclic group, or combination of aliphatic and cyclic groups (e.g., alkaryl and aralkyl groups). In the context of the present disclosure, suitable organic groups for the compounds described herein are those that do not interfere with the hydropersulfide generating activity of the compounds. In the context of the present disclosure, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "alkoxy" refers to an —O-alkyl group, wherein alkyl is as defined above. Examples include, but are not limited to, methoxy, ethoxy, n-propyloxy, propyloxy, n-butyloxy, i-butyloxy, t-butyloxy. "Lower alkoxy" as used herein denotes an alkoxygroup with a "lower alkyl" group as previously defined.

The term "aryl" as used herein includes carbocyclic aromatic rings or ring systems. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The disclosure is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

A subject, as defined herein, is an animal such as a vertebrate or invertebrate organism. In some aspects, the subject is a single celled organism such as a yeast or bacteria. In other aspects, the subject is a mammal such as a domesticated farm animal (e.g., cow, horse, pig) or pet (e.g., dog, cat). More preferably, the subject is a human.

Treat", "treating", and "treatment", etc., as used herein, refer to any action providing a benefit to a subject afflicted with a disease or condition involving hydropersulfides, such as inflammation or ischemia, including improvement in the condition through lessening or suppression of at least one symptom, delay in progression of the disease, etc.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as improving hydropersulfide levels by a detectable amount.

Hydropersulfide Precursors

In one aspect, the present disclosure provides a hydropersulfide precursor compound having the formula (I):

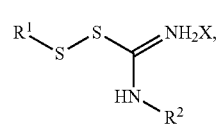

wherein R$^1$ is a C$_1$-C$_6$ alkyl group optionally substituted with one or more of a carboxylic acid, C(O)OR$^a$, NHC(O)R$^b$, NHC(O)(CH$_2$)$_2$CH(NHC(O)R$^c$)(COOR$^d$), NHC(O)(CH$_2$)$_2$CH(NH$_2$)(COOR$^d$), C(O)NHCH$_2$COOR$^e$, and a phenyl group optionally substituted with a lower alkyl, lower alkoxy, or trifluoromethyl moiety;

$R^2$ is H, a $C_1$-$C_6$ alkyl moiety, or a $C_6$-$C_{10}$ aryl group that is optionally substituted with a halogen, lower alkyl, lower alkoxy, or trifluoromethyl moiety;

X is a halogen; and wherein $R^a$ is a $C_1$-$C_{20}$ alkyl moiety or a peptide chain comprising of 1-5 amino acids;

$R^b$ is a $C_1$-$C_{20}$ alkyl moiety;

$R^c$ is a $C_1$-$C_{20}$ alkyl moiety;

$R^d$ is H, a $C_1$-$C_{20}$ alkyl moiety, or a peptide chain comprising of 1-5 amino acids; and $R^e$ is H or a $C_1$-$C_{20}$ alkyl moiety.

In another aspect, the present disclosure provides a hydropersulfide precursor compound having the formula (I):

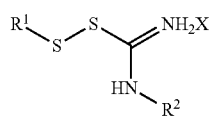

(I)

wherein $R^1$ is a $C_1$-$C_6$ alkyl group optionally substituted with one or more of a carboxylic acid, $C(O)OR^a$, and $NHC(O)R^b$;

$R^2$ is H, $C_1$-$C_6$ alkyl moiety or a $C_6$-$C_{10}$ aryl group that is optionally substituted with a halogen, methyl, methoxy, or trifluoromethyl moiety;

X is a halogen; and wherein $R^a$ is a $C_1$-$C_{20}$ alkyl moiety; and $R^b$ is a $C_1$-$C_{20}$ alkyl moiety.

In certain instances $R^a$ is a lower alkyl moiety. In further instances $R^a$ is methyl. In other instances $R^b$ is a lower alkyl moiety. In further instances $R^b$ is methyl.

The inventors have shown that the $R^1$ alkyl group of the hydropersulfide precursor compound can vary substantially without loss of the ability of the compound to serve as a hydropersulfide precursor. In some instances, $R^1$ is a group having the formula (II):

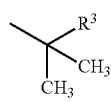

(II)

wherein $R^3$ is selected from methyl, ethyl, propyl,

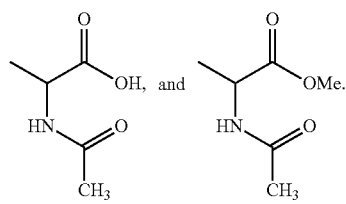

In further instances, $R^1$ is

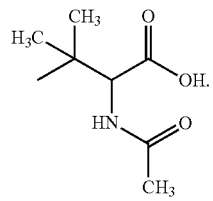

In other instances $R^1$ is

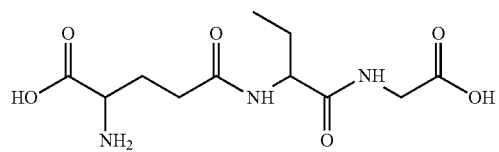 [SMILES: CCC(NC(=O)CCC(N)C(=O)O)C(=O)NCC(=O)O]

In even further instances $R^1$ may be one of the following:

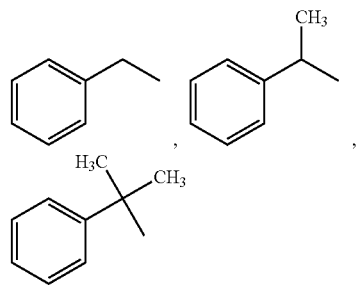

wherein the phenyl group may be unsubstituted or substituted with a lower alkyl, lower alkoxy, or trifluoromethyl moiety.

In some aspects, $R^2$ is a phenyl group that is optionally substituted with a halogen, methyl, methoxy, or trifluoromethyl moiety. In further aspects, $R^2$ is a phenyl group substituted with a halogen or trifluoromethyl moiety. It has been discovered that hydropersulfide precursors including an aryl ring having electron withdrawing substituents exhibit higher hydropersulfide yields and half-lives.

In some instances the hydropersulfide precursor compound is selected from compounds 4a-h as shown in FIG. 1.

Preparation of Hydropersulfide Precursor Compounds

The compounds described herein may be synthesized by synthetic routes that include processes analogous to those well known in the chemical arts, particularly in light of the description contained herein. The starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.) and similar texts known to those skilled in the art.

In one aspect, the present disclosure provides a process for preparing a hydropersulfide precursor compound having the formula (I):

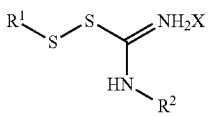

wherein wherein $R^1$ is a $C_1$-$C_6$ alkyl group optionally substituted with one or more of a carboxylic acid, $C(O)OR^a$, $NHC(O)R^b$, $NHC(O)(CH_2)_2CH(NHC(O)R^c)(COOR^d)$, $NHC(O)(CH_2)_2CH(NH_2)(COOR^d)$, $C(O)NHCH_2COOR^e$, and a phenyl group optionally substituted with a lower alkyl, lower alkoxy, or trifluoromethyl moiety;

$R^2$ is H, a $C_1$-$C_6$ alkyl moiety, or a $C_6$-$C_{10}$ aryl group that is optionally substituted with a halogen, lower alkyl, lower alkoxy, or trifluoromethyl moiety;

X is a halogen; and wherein $R^a$ is a $C_1$-$C_{20}$ alkyl moiety or a peptide chain comprising of 1-5 amino acids;

$R^b$ is a $C_1$-$C_{20}$ alkyl moiety;

$R^c$ is a $C_1$-$C_{20}$ alkyl moiety;

$R^d$ is H, a $C_1$-$C_{20}$ alkyl moiety, or a peptide chain comprising of 1-5 amino acids; and $R^e$ is H or a $C_1$-$C_{20}$ alkyl moiety.

The process includes coupling an alkyl thiol compound having formula (III):

with an N-substituted thiourea compound having formula (IV):

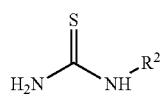

under acidic conditions in the presence of hydrogen peroxide to form the hydropersulfide precursor compound having formula (I).

The process can be used to prepare any of the hydropersulfide precursors described herein.

An example of the process that can be used to prepare the hydropersulfide precursor compounds is provided in Example 2 herein. An equivalent amount of alkyl thiol is combined with N-substituted thiourea in a polar solvent (e.g., ethanol) and cooled below room temperature (e.g., to about 0° C.). The solution is then acidified by adding a concentrated acid (e.g., hydrochloric acid) and water. A peroxide (e.g., hydrogen peroxide) is then added and the mixture is stirred while remaining chilled. In some embodiments, an amount of hydrogen peroxide is present that is about equimolar or slightly in excess of equimolar with the concentration of the alkyl thiol. The resulting S-substituted thioisothiourea is then purified (e.g., by flash chromatography).

Generation of Hydropersulfide Using Hydropersulfide Precursor Compounds

In another aspect, the present disclosure provides a method of generating a hydropersulfide. The method involves using one of the hydropersulfide precursor compounds to generate a hydropersulfide (i.e., R-S-S-H). The method of generating a hydropersulfide can include contacting a hydropersulfide precursor compound having the formula (I):

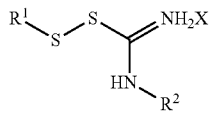

wherein $R^1$ is a $C_1$-$C_6$ alkyl group optionally substituted with one or more of a carboxylic acid, $C(O)OR^a$, $NHC(O)R^b$, $NHC(O)(CH_2)_2CH(NHC(O)R^c)(COOR^d)$, $NHC(O)(CH_2)_2CH(NH_2)(COOR^d)$, $C(O)NHCH_2COOR^e$, and a phenyl group optionally substituted with a lower alkyl, lower alkoxy, or trifluoromethyl moiety;

$R^2$ is H, a $C_1$-$C_6$ alkyl moiety, or a $C_6$-$C_{10}$ aryl group that is optionally substituted with a halogen, lower alkyl, lower alkoxy, or trifluoromethyl moiety;

X is a halogen; and wherein $R^a$ is a $C_1$-$C_{20}$ alkyl moiety or a peptide chain comprising of 1-5 amino acids;

$R^b$ is a $C_1$-$C_{20}$ alkyl moiety;

$R^c$ is a $C_1$-$C_{20}$ alkyl moiety;

$R^d$ is H, a $C_1$-$C_{20}$ alkyl moiety, or a peptide chain comprising of 1-5 amino acids; and $R^e$ is H or a $C_1$-$C_{20}$ alkyl moiety with an aqueous solution.

Hydropersulfide generation can be carried out using any of the hydropersulfide precursors described herein.

The hydropersulfide precursor compounds described herein can provide efficient and controllable release of hydropersulfides under physiological conditions. Accordingly, in some aspects the hydropersulfide is generated in vivo. However, the hydropersulfide precursor compounds can be used to generate hydropersulfides under non-physiological conditions as well, and can be used to generate hydropersulfide in vitro.

Because hydrogen sulfide and hydropersulfide are biologically important signaling molecules, the hydropersulfide precursor compounds can be used to treat subjects having a disease or disorder where increased hydropersulfide formation would be beneficial. For example, in some insances, the hydropersulfide is generated in a therapeutically effective amount in a subject in need of smooth muscle relaxation, inhibition of inflammation, or cardioprotection. When used for treatment, the hydropersulfide precursor compounds can be provided in a pharmaceutically acceptable carrier or other suitable formulation.

The present disclosure is illustrated by the following examples. It is to be understood that the particular examples, materials, amounts, and procedures are to be interpreted broadly in accordance with the scope and spirit of the disclosure as set forth herein.

EXAMPLES

Example I: Development of S-Substituted Thioisothioureas as Efficient Hydropersulfide Precursors A general strategy for RSSH generation is to substitute the terminal sulfhydryl group with a suitable protecting group. The reaction of alkyl halides with thiourea is a commonly used method for thiol synthesis (Scheme 2, eq. 1). Cossar et al., J. Org. Chem., 27, 93-95 (1962). This multistep one-pot process proceeds via the intermediacy of an isothiourea, which is then hydrolyzed under basic condition to produce the desired thiol and urea as a byproduct. Rad, M. N. S.; Maghsoudi, S., RSC Adv., 6, 70335-70342 (2016).

In view of this known reaction, it was thought that the terminal sulfhydryl group of RSSH could be protected in the form of an S-alkylthioisothiourea (Scheme 2, eq. 2), which could then potentially be deprotected under physiological condition to produce RSSH. It was expected that the more acidic nature of RSSH vs. RSH should facilitate RSSH release. In this design, thiols are used to construct the RSSH precursors in a convenient one-pot process. It was also anticipated that different thiol and thiourea substituents could potentially affect the rates of deprotection, thereby offering tunability of RSSH release.

Scheme 2. Design of S-Substituted-Thioisothioureas as Hydropersulfide Precursors

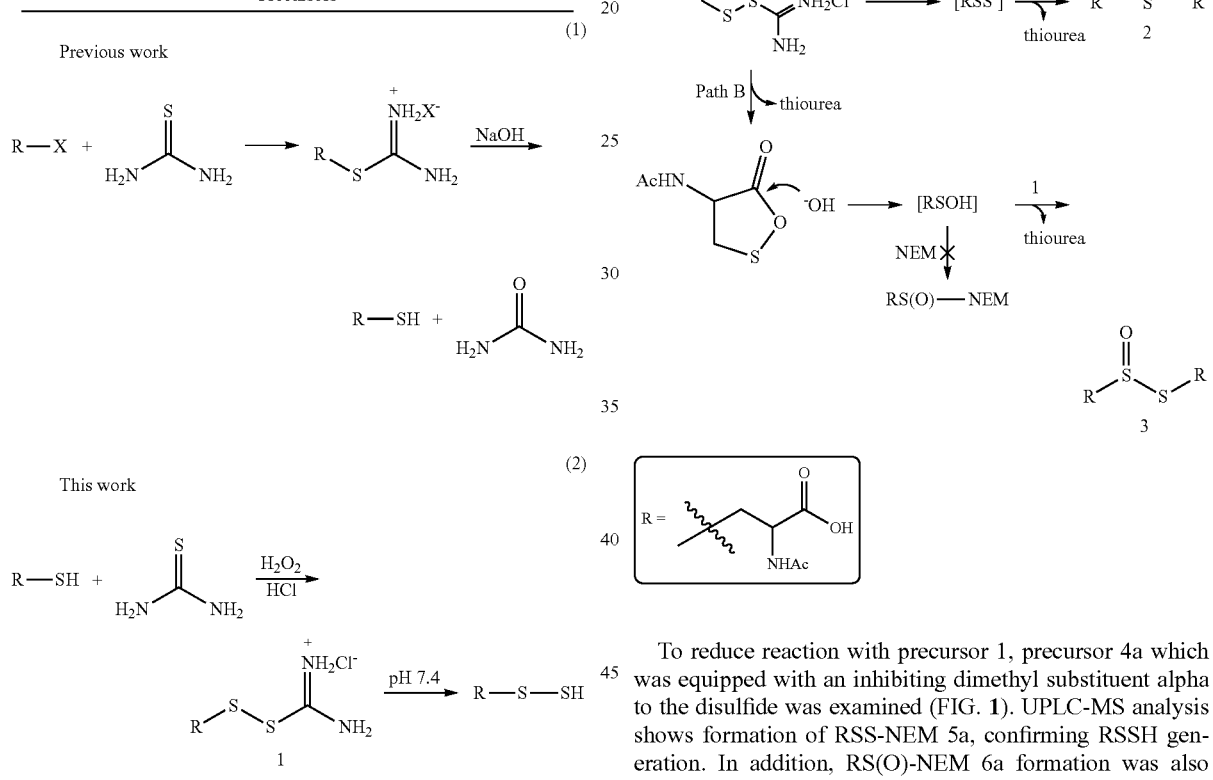

Scheme 3. Proposed Mechanism of Trisulfide 2 and Thiosulfinate 3 Formation from Precursor 1

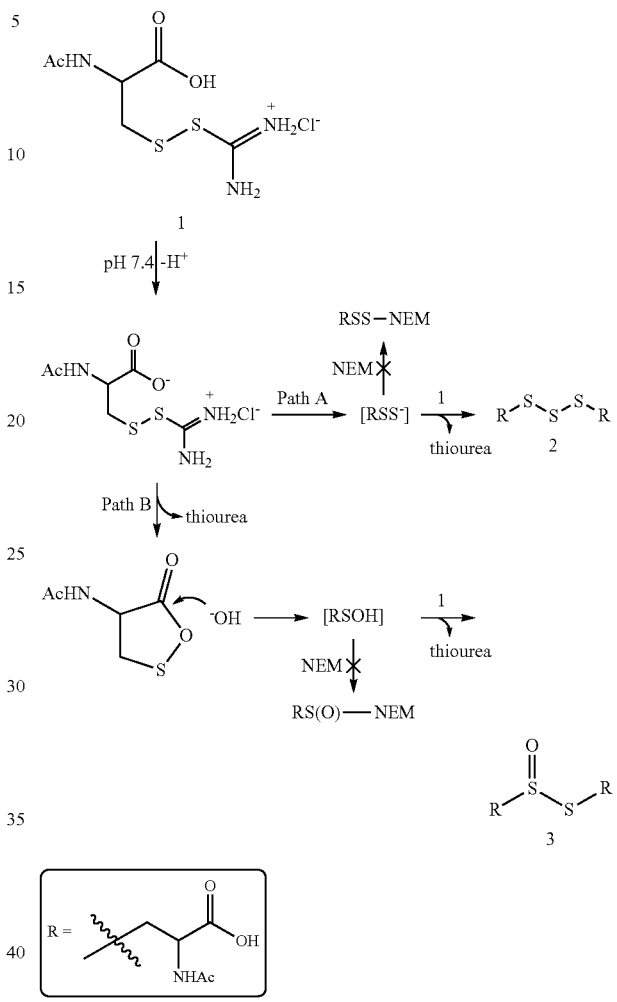

Figure 5:
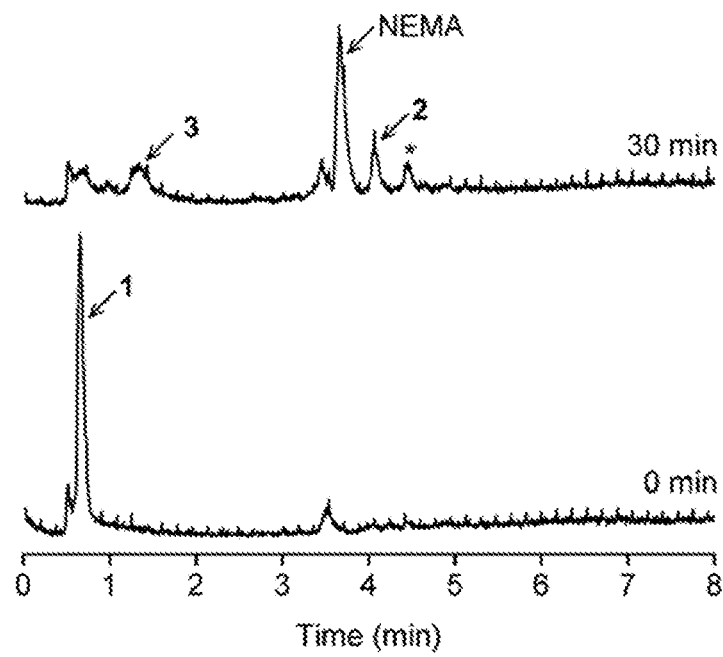
FIG. 5 provides a graph of UPLC-MS chromatograms of RSSH generation from compound 1 (1 mM) in the presence of NEM (5 mM) incubated in pH 7.4 ammonium bicarbonate buffer containing DTPA (100 μM) for 30 min at 37° C. The asterisk indicates the methyl ester analogue of dialkyl trisulfide 2, which was also formed due to the presence of minor amount of methyl ester analogue of 1. A peak at 3.7 min corresponding to N-ethylmaleamic acid (NEMA), derived from NEM hydrolysis, was observed under these conditions.
Figure 6:
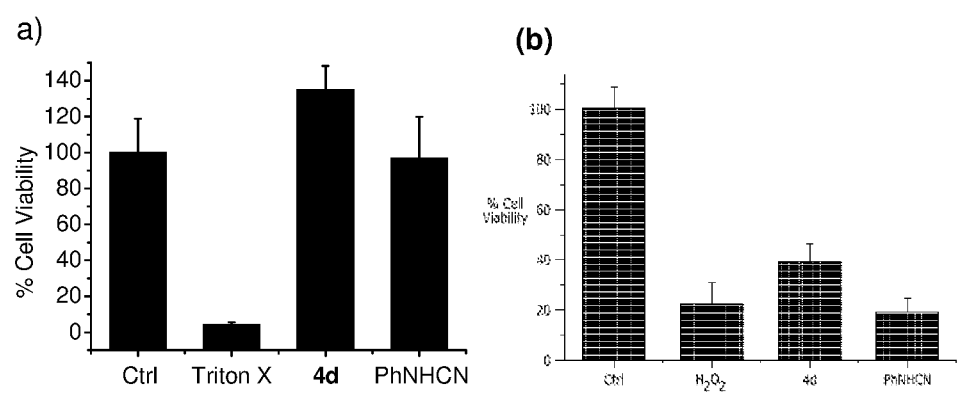
FIGS. 6a and 6b provide graphs of (a) the cell viability of cardiomyocyte H9c2 cells following incubation of the RSSH precursor 4d (50 μM) and phenylcynamide (200 μM) for 24 h; and (b) the cytoprotective effects of the RSSH precursor 4d observed following pretreatment of H9c2 cells with either 4d (50 μM) or phenylcynamide (200 μM) for 2 h, followed by hydrogen peroxide (200 μM) treatment for 2 h. Quantification of cell viability was carried out using Cell Counting Kit-8 (CCK-8). Results are expressed as the mean±SEM (n=6).

To test this hypothesis, precursor 1 was synthesized (Scheme 2, eq. 2), and RSSH generation was examined using N-ethylmaleimide (NEM) as a trap. The RSS-NEM adduct was monitored by ultra-performance liquid chromatography-mass spectrometry (UPLC-MS). Incubation of 1 with NEM in pH 7.4 buffer at 37° C. for 30 min led to complete disappearance of 1, with no evidence of persulfide-NEM adduct formation. Instead, formation of dialkyltrisulfide 2 was observed (FIG. 5). Precursor 1 does indeed produce RSSH; however, due to the more electrophilic nature of the precursor itself compared with NEM, RSSH reacts preferentially with 1 to produce trisulfide 2 (Scheme 3, Path A). In addition, thiosulfinate RS(O)-SR 3 was also observed as a major product (FIG. 5), suggesting an intramolecular cyclization mechanism and subsequent production of a sulfenic acid (RSOH) intermediate that is also trapped by precursor 1 (Scheme 3, Path B).

To reduce reaction with precursor 1, precursor 4a which was equipped with an inhibiting dimethyl substituent alpha to the disulfide was examined (FIG. 1). UPLC-MS analysis shows formation of RSS-NEM 5a, confirming RSSH generation. In addition, RS(O)-NEM 6a formation was also obvserved indicating that the RSOH-producing reaction (Scheme 4, Path B) remains competitive with the desired production of RSSH (Path A).

Next, precursor 4b, equipped with methyl group on the nitrogen of the thiourea moiety, was synthesized to examine the effect of N-alkyl substituents on RSSH generation. The RSSH yield was reduced compared with that from 4a (SI, Figure S18), suggesting that an alkyl substituent on nitrogen disfavors RSSH generation and RSOH generation remains the dominant reaction path.

To prevent sulfenic acid generation from a carboxylic acid-mediated intramolecular cyclization, precursor 4c in which the carboxylic acid was masked as methyl ester was examined Although decomposition of 4c in the presence of NEM produced no evidence of RS(O)-NEM 6b formation, RSS-NEM adduct 5b is formed in less than 50% yield with other products also observed.

Scheme 4. Proposed Mechanism of Precursors 4a-c Decomposition in the Presence of NEM

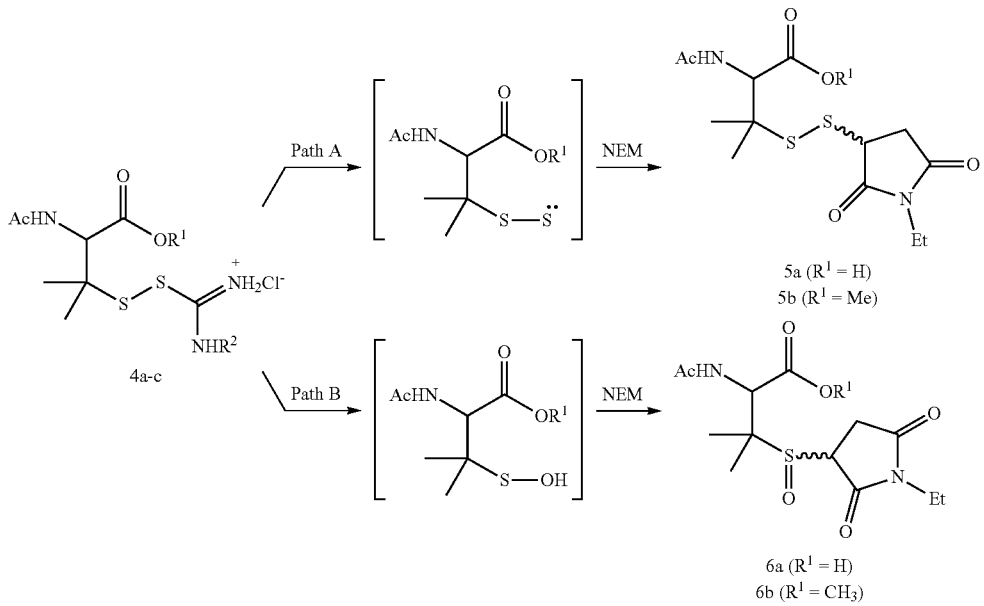

Next, precursor 4d in which the thiourea is substituted with a phenyl group was examined Analysis of RSSH generation from 4d in the presence of NEM shows clean conversion of 4d to the RSS-NEM adduct 5a with no evidence of the sulfenic acid-derived product 6a. Based on the mechanism of isothiourea hydrolysis which produces alkyl thiol and urea (Scheme 2, eq. 1), it was expected that N-phenylurea would be formed in high yield. However, UPLC-MS analysis showed no evidence of N-phenylurea, indicating that hydrolysis is not the operative mechanism for RSSH generation. Instead, phenyl cyanamide is observed in 94% yield, indicating an elimination mechanism for RSSH generation (see Scheme 5).

Figure 2:
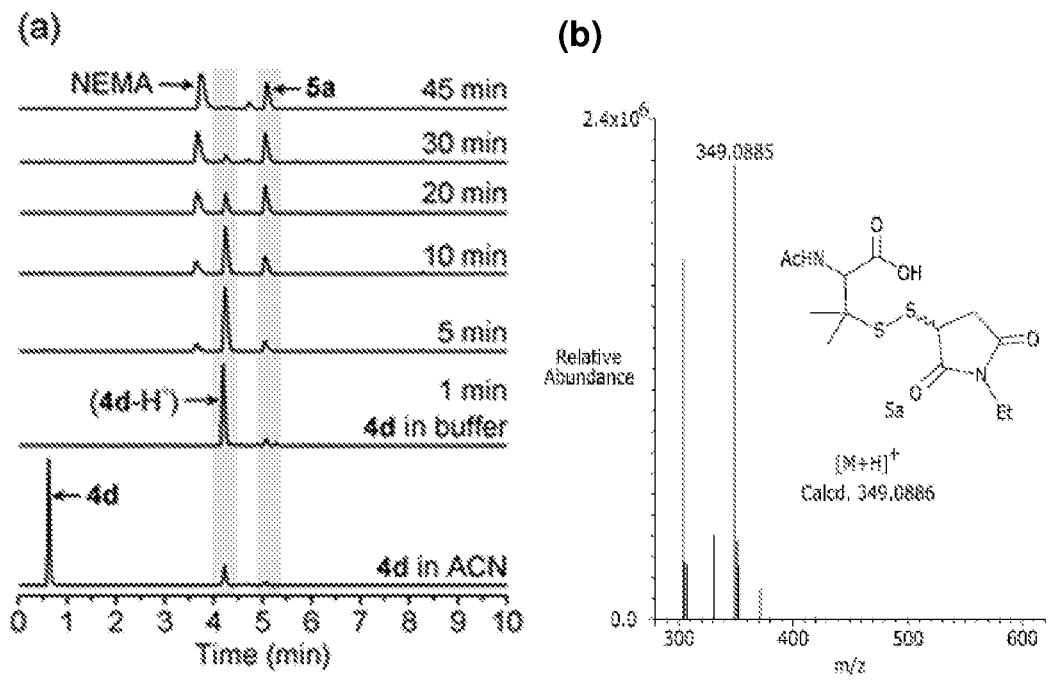
FIGS. 2a and 2b provide graphs of (a) UPLC-MS chromatograms of RSSH generation from 4d (200 μM) in the presence of NEM (4 mM) incubated in pH 7.4 ammonium bicarbonate (100 mM) with DTPA (100 μM) at 37° C. A peak at 3.7 min corresponding to N-ethylmaleamic acid (NEMA), derived from NEM hydrolysis, was observed under these conditions (see SI); (b) MS spectrum (ESI+ mode) of the product eluting at 5.06 min corresponding to 5a with m/z 349.0885 (expected m/z 349.0886).

To gain additional insight into the mechanism of RSSH formation, 4d was analyzed by UPLC-MS in acetonitrile. Here, a peak at 0.66 minutes was observed (FIG. 2a, bottom trace). Immediately following introduction of 4d to pH 7.4 buffer, this peak disappears with concomitant appearance of a new peak at 4.2 minutes which is assigned to the neutral form of 4d (4d-H$^+$). This result suggests that precursor 4d rapidly undergoes neutralization at pH 7.4 to form an intermediate 4d-H$^+$, which then decomposes to release RSSH and phenyl cyanamide. RSSH generation from 4d was also confirmed using iodoacetamide (IAM), another commonly used RSSH trap. Together, these results confirm the improved ability of 4d to produce RSSH.

Figure 3:
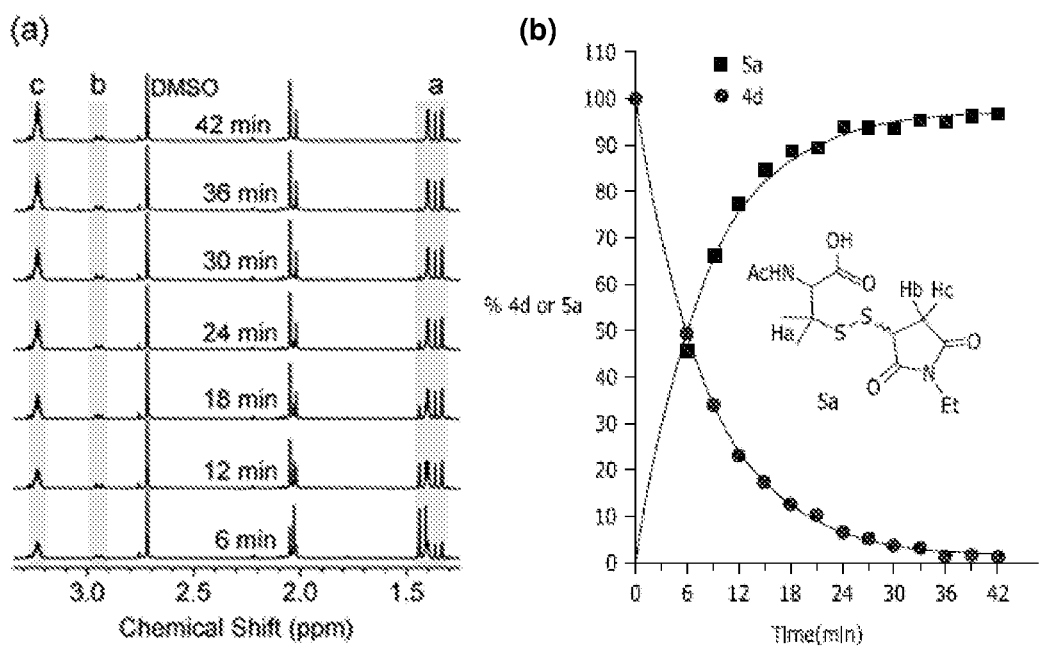
FIGS. 3a and 3b provide graphs of (a) Stacked $^1$H NMR spectra showing the decomposition of precursor 4d (1 mM) with NEM (20 mM) in 10% $D_2O$, phosphate buffer (PB), pH 7.4 at 37° C. to produce RSS-NEM adduct 5a; Precursor 4d was introduced to a solution of NEM in PB at t=0 min and following equilibration and shimming, the first 1H NMR spectrum was obtained after 6 min.; and (b) The kinetics of decomposition of 4d (circles represent the —$CH_3$ protons ($H_a$) of the precursor) and formation of 5a (squares represent the diasterotopic protons ($H_b$) of the succinimide ring of the two product diastereomers). The curves are calculated best fits to a single-exponential function (k=0.12 min$^{-1}$ and $t_{1/2}$=5.6 min for each fit).

Next, $^1$H NMR spectroscopy was used to monitor the kinetics of RSSH generation from 4d by trapping with NEM in 10% D$_2$O, pH 7.4 buffer containing DMSO as an internal standard at 37° C. An increase in the peak intensity attributed to one of the diasterotopic protons of the succinimide ring of the two product diastereomers (H$_b$, δ2.99-2.91 ppm) was observed (FIG. 3a). The other diasterotopic proton (H$_c$, δ3.30-3.21 ppm) overlaps with N-ethylmaleamic acid (NEMA), a product derived from NEM hydrolysis. Similarly, the intensity of two methyl group protons of precursor 4d (δ1.44 and 1.41 ppm) decreased as four methyl group protons of the two diastereomers of 5a (H$_a$, δ1.40, 1.37 ppm and 1.40, 1.34 ppm) increased, supporting the clean conversion of 4d to 5a. The $^1$H NMR peak assignments for 5a are consistent with the RSS-NEM adduct formed during S-methoxycarbonyl penicillamine disulfide (MCPD) decomposition (Scheme 1, eq. 3) in the presence of NEM. The half-life of precursor 4d at 37° C. is 5.6 min with a 96% yield of RSS-NEM adduct 5a (FIG. 3b).

Precursor 4e, equipped with a 4-OMe substituent, was synthesized to study the effect of an electron donating group on the phenyl ring. The half-life of 4e was found to be 5.0 min (Table 1), suggesting no significant effect on the kinetics of RSSH generation. However, the RSSH yield (75%) was reduced and sulfenic acid-derived product 6a is now observed, suggesting that an electron donating group on the phenyl ring disfavors RSSH generation. In contrast, we find that electron withdrawing substituents maintain efficient RSSH generation, with a small effect on the kinetics of RSSH release. For example, 2-Cl substituted precursor 4f produces RSS-NEM in 95% yield with a 17.3 min half-life, and 4-Cl substituted precursor 4g produces the NEM adduct in 91% with a 9.3 min half-life. Similarly, 4-CF$_3$ substituted precursor 4h produces 95% of RSS-NEM with a half-life of 6.8 min.

TABLE 1

Hydropersulfide yields and half-lives for Precursors 4d-h

| Precursor | R$^1$ | R$^2$ | Hydropersulfide Yield (%)$^a$ | t$_{1/2}$ (min)$^b$ |
|---|---|---|---|---|
| 4d | H | Ph | 96 ± 1 | 5.6 ± 0.3$^c$ |
| 4e | H | 4-MeOPh | 75 ± 2 | 5.0 ± 0.5 |
| 4f | H | 2-ClPh | 95 ± 2 | 173 ± 0.4 |
| 4g | H | 4-ClPh | 91 ± 1 | 9.3 ± 0.6 |
| 4h | H | 4-CF$_3$Ph | 95 ± 2$^d$ | 6.8 ± 0.2$^d$ |

$^a$RSSH yield was calculated based upon % precursor consumed.
$^b$RSSH precursors (1 mM) were incubated in the presence of NEM (20 mM) in pH 7.4 phosphate buffer containing 10% D$_2$O at 37° C.
$^c$The half-life of 4d is 4.3 min in pH 7.4 buffer with 20% MeOD.
$^d$Reduced aqueous solubility required this experiment to be carried out in pH 7.4 buffer with 20% MeOD.

Based on the clean formation of hydropersulfide and aryl cyanamide during decomposition of 4d-h, the general mechanism shown in Scheme 5 is proposed. Neutralization of S-alkyl-thioisothiourea 7 (or its resonance partner 7a) occurs at pH 7.4 to produce a neutral species 8 and/or 8a, which can further undergo an elimination reaction to produce RSSH and aryl cyanamide. The elimination reaction can be initiated by either donation of the imine-nitrogen lone pair of 8 to form aryl cyanamide and RSSH (Scheme 5, eq. 2) or deprotonation of the arylamino-nitrogen proton to form RSSH and an aryl carbodiimide, which can further undergo tautomerization to afford the aryl cyanamide (Scheme 5, eq. 3). Alternately, an elimination reaction can be initiated by donation of the nitrogen lone pair of intermediate 8a to produce RSSH and aryl carbodiimide (Scheme 5, eq. 1). The decomposition of precursor 4d was examined at pH 6 and pH 8.5. Decomposition is substantially slowed at lower pH and increased at higher pH, consistent with the mechanism proposed in Scheme 5. The reduced RSSH yield from methoxy-substituted 4e suggests that an electron donating group on the phenyl ring disfavors neutralization to form 8/8a, and as a result carboxylate anion attack of the disulfide to produce sulfenic acid can contribute. Slower RSSH generation from 4f-h suggests that an electron withdrawing group on the phenyl ring might cause the nitrogen lone pair (e.g., in 8a) to be less available for the elimination reaction. In addition, the thermodynamic stability of the aryl cyanamide produced could contribute to the observed rate of RSSH release.

from 9 compared with 4d suggests additional influence of the S-alkyl substituent on RSSH generation.

Example II: Cytotoxicity and Cell Viability Studies

The cytotoxicity and impact on cell viability of the hydropersulfide (RSSH) precursor 4d have been examined using the cardiomyocyte H9C2 cell line and Cell Counting Kit-8 (CCK-8). A cell viability assay reveled that 4d was not cytotoxic at 50 µM (FIG. 1a). In addition, the byproduct of RSSH release, phenyl cyanamide (PhNHCN), is observed to be well tolerated by H9c2 cells up to 200 µM under similar conditions.

Since hydropersulfides are reported to mitigate oxidative stress, the ability of RSSH precursor 4d to protect cardiomyocyte H9c2 cells from cytotoxicity induced by hydrogen peroxide ($H_2O_2$) was tested. Significant cell killing was found following treatment with 200 µM of hydrogen peroxide; hence this concentration was chosen to study the possible cytoprotective effects of RSSH precursor 4d. When H9c2 cells were pretreated with 4d for two hours, significant cytoprotection was observed (FIG. 1b). Notably, the byproduct of RSSH formation from 4d, phenyl cyanamide, did not protect cells from $H_2O_2$-induced cytotoxicity, supporting the involvement of RSSH in the observed cytoprotective effects.

In summary, S-substituted-thioisothioureas have been designed, synthesized, and evaluated as RSSH precursors. These precursors show efficient and controllable release of RSSH under physiological conditions. It has also been Scheme 5. Proposed Mechanism of Hydropersulfide Generation from S-substituted Thioisothioureas.

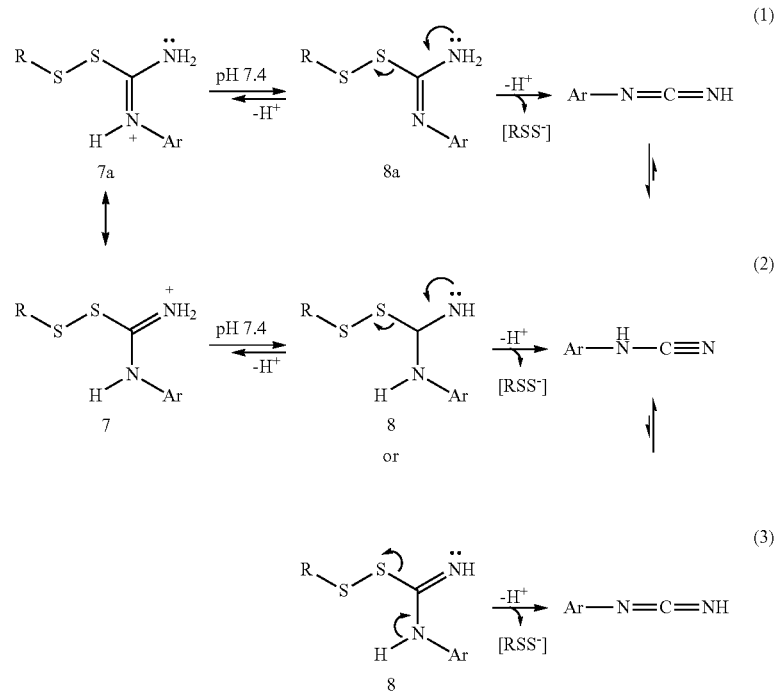

Figure 4:
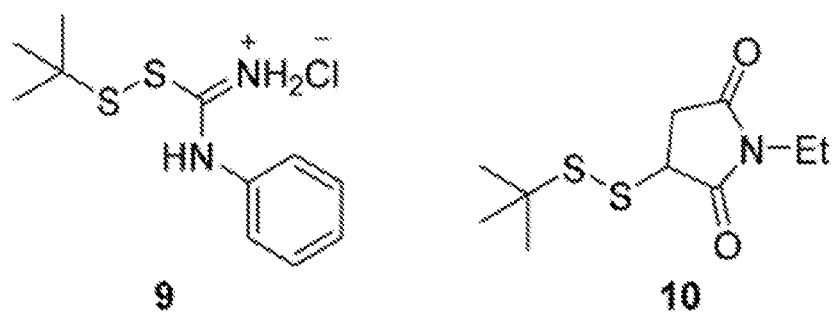
FIG. 4 provides the chemical structures of Precursor 9 and RSS-NEM adduct 10.

To demonstrate the generality of S-substituted thioisothioureas as hydropersulfide precursors, tert-butylthiol-based precursor 9 (FIG. 4), which produces a near quantitative yield (97%) of RSS-NEM adduct 10 with a half-life of 17.3 min was also examined. Slower RSSH generation observed demonstrated that RSSH generation can be tuned by structural modifications. Importantly, these precursors are found to be stable for several months on the bench-top in the solid state and for a few weeks in $D_2O$ at room temperature. Given the significance of RSSH in redox biology, these S-substi-

Example III: Preparation of S-Substituted Thioisothioureas

All starting materials were of reagent grade and used without further purification. N-acetyl-D-penicillamine, N-ethylmaleimide, N-ethylmaleamic acid, and phenylcyanamide were purchased from Sigma-Aldrich and used without further purification. Thiourea and N-substituted thioureas were purchased from Alfa Aesar and Oakwood Chemicals. Deuterated solvents (Cambridge Isotope Laboratories) were used for NMR spectroscopic analyses. NMR spectra were obtained on a 400 MHz FT-NMR spectrometer. All chemical shifts are reported in parts per million (ppm) relative to residual $CHCl_3$ (7.26 ppm for $^1H$, 77.2 ppm for $^{13}C$), residual $H_2O$ (4.79 ppm for $^1H$), residual DMSO (2.50 ppm for $^1H$, 39.5 for $^{13}C$), or residual MeOH (3.31 ppm for $^1H$, 49.2 ppm for $^{13}C$). The kinetics of RSSH generation were measured using a Varian Inova 800 MHz spectrometer. UPLC-MS analysis was carried out with a Waters Acquity/Xevo-G2 UPLC-MS system equipped with an ACQUITY UPLC BEH C18 column (2.1 mm×50 mm, 1.7 μm). The mass signals for products of hydropersulfide trapping with NEM were obtained via deconvolution using MassLynx 4.1 software. The pH measurements were performed using a Fisher Scientific Accumet AB15 pH-meter. Analytical thin layer chromatography (TLC) was performed on Sigma-Aldrich silica gel on TLC Al foils with fluorescent indicator F254 plates. Visualization was accomplished with UV light (254 nm) or staining with $KMnO_4$. Flash column chromatography was performed using SiliaFlash P60 (230-400 mesh) silica gel. Melting points were recorded using MEL-TEMP® capillary melting point apparatus and are uncorrected.

Experimental Procedures

General procedure for synthesis of S-substituted-thioisothioureas (Yin et al, Brain Res., 1491, 188-196 (2013).

Alkyl thiol (1 mmol) and N-substituted thiourea (1 mmol) were dissolved in ethanol (10 mL) and cooled to 0° C. To this solution, concentrated hydrochloric acid (0.2 mL) and water (0.2 mL) were carefully added. Hydrogen peroxide (30%, 1.1 mmol) was added dropwise and the resulting mixture was stirred at 0° C. for 1 h. All volatiles were removed under reduced pressure and the product was isolated by flash chromatography (dichloromethane/methanol) on silica gel.

((2-acetamido-2-carboxyethyl)disulfaneyl)(amino) methaniminium chloride 1:

Hydropersulfide precursor 1 was synthesized using the general procedure described above. However, the methyl ester analogue of 1 was also obtained in 9% yield during the synthesis of 1. Several attempts at purification were unsuccessful. This mixture was obtained as white solid, mp=70-72° C., 381 mg, 76% combined yield.

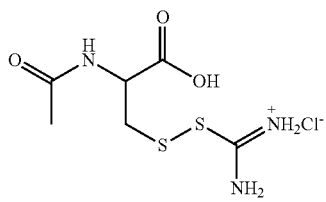

$^1H$ NMR (400 MHz, DMSO-$d_6$) δ9.80 (bs, 2H), 9.43 (bs, 2H), 8.57 (d, J=8.1 Hz, 1H), 4.51-4.49 (m, 1H), 3.26-3.14 (m, 2H), 1.88 (s, 3H); $^{13}C$ NMR (101 MHz, DMSO-$d_6$) δ171.3, 169.7, 169.1, 51.2, 41.1, 22.4; HRMS (ESI): m/z calcd. for $C_6H_{12}N_3O_3S_2^+[M]^+$238.0315, found 238.0312.

((2-acetamido-3-methoxy-3-oxopropyl)disulfaneyl) (amino)methaniminium chloride:

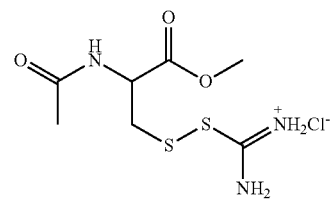

$^1H$ NMR (400 MHz, DMSO-$d_6$) δ9.80 (bs, 2H), 9.43 (bs, 2H), 8.72 (d, J=8.1 Hz, 1H), 4.60-4.56 (m, 1H), 3.65 (s, 3H), 3.26-3.14 (m, 2H), 1.88 (s, 3H); HRMS (ESI): m/z calcd. for $C_7H_{14}N_3O_3S_2^+[M]^+$252.0471, found 252.0473.

((1-acetamido-1-carboxy-2-methylpropan-2-yl)disulfaneyl)(amino)methaniminium chloride 4a:

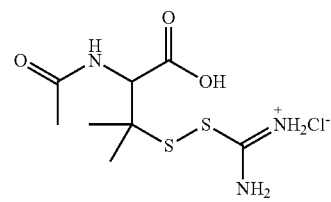

White solid, mp=154-156° C., 394 mg, 83% yield, $^1H$ NMR (400 MHz, DMSO-$d_6$) δ9.78 (bs, 2H), 9.46 (bs, 2H), 8.47 (d, J=9.3 Hz, 1H), 4.55 (d, J=9.3 Hz, 1H), 1.92 (s, 3H), 1.38 (s, 3H), 1.37 (s, 3H); $^{13}C$ NMR (101 MHz, DMSO-$d_6$) δ170.6, 169.8, 169.5, 57.9, 54.9, 24.3, 22.7, 22.3; HRMS (ESI): m/z calcd. for $C_8H_{16}N_3O_3S_2^+[M]^+$266.0628, found 266.0622.

((1-acetamido-1-carboxy-2-methylpropan-2-yl)disulfaneyl)(methylamino) methaniminium chloride 4b:

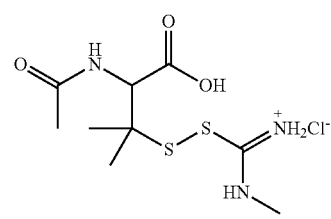

White solid, mp=153-155° C., 420 mg, 85% yield, $^1H$ NMR (400 MHz, DMSO-$d_6$) δ9.84 (bs, 2H), 9.60 (s, 1H), 8.50 (d, J=9.2 Hz, 1H), 4.55 (d, J=9.2 Hz, 1H), 2.98 (s, 3H), 1.93 (s, 3H), 1.38 (s, 3H), 1.37 (s, 3H); $^{13}C$ NMR (101 MHz, DMSO-$d_6$) δ170.6, 169.8, 165.6, 58.0, 54.9, 31.3, 24.5, 22.7, 22.3; HRMS (ESI): m/z calcd. for $C_9H_{18}N_3O_3S_2^+[M]^+$280.0784, found 280.0783.

Methyl 2-acetamido-3-mercapto-3-methylbutanoate: (Nicholson et al., Pharmacol. Res., 62, 289-297 (2010).

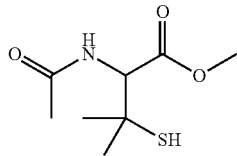

To an ice-cooled solution of N-acetylpenicillamine (500 mg, 2.61 mmol) in anhydrous methanol (10 mL), thionyl chloride (0.28 mL, 3.92 mmol) was added dropwise under a nitrogen atmosphere. The resulting solution was heated at 40° C. for 1 h and then the volatiles were removed under reduced pressure. The crude material was purified using silica gel column chromatography using 1% MeOH in dichloromethane as the eluent. This compound was obtained as white solid, 110 mg, 21% yield, $^1$H NMR (400 MHz, CDCl$_3$) δ6.37 (d, J=9.0 Hz, 1H), 4.65 (d, J=9.0 Hz, 1H), 3.75 (s, 3H), 2.07 (s, 3H), 1.98 (d, J=1.3 Hz, 1H), 1.49 (s, 3H), 1.36 (d, J=1.1 Hz, 3H).

((3-acetamido-4-methoxy-2-methyl-4-oxobutan-2-yl)disulfaneyl)(amino)methaniminium chloride 4c:

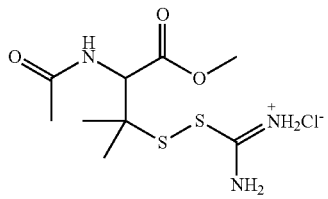

White solid, mp=190-192° C., 135 mg, 63% yield, $^1$H NMR (400 MHz, DMSO-d$_6$) δ9.54 (bs, 4H), 8.58 (d, J=9.1 Hz, 1H), 4.65 (d, J=9.1 Hz, 1H), 3.68 (s, 3H), 1.93 (s, 3H), 1.37 (s, 6H); $^{13}$C NMR (101 MHz, DMSO-d$_6$) δ169.9, 169.7, 169.2, 57.8, 54.7, 52.2, 23.9, 22.6, 22.2; HRMS (ESI): m/z for C$_9$H$_{18}$N$_3$O$_3$S$_2^+$[M]$^+$ calcd. 280.0784, found 280.0788.

((1-acetamido-1-carboxy-2-methylpropan-2-yl)disulfaneyl)(phenylamino)methaniminium chloride 4d:

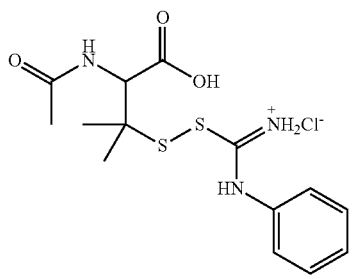

White solid, mp=155-157° C., 515 mg, 87% yield, $^1$H NMR (400 MHz, DMSO-d$_6$) δ8.47 (d, J=9.2 Hz, 1H), 7.53-7.49 (m, 2H), 7.43-7.35 (m, 3H), 4.61 (d, J=9.2 Hz, 1H), 1.92 (s, 3H), 1.45 (s, 3H), 1.41 (s, 3H); $^{13}$C NMR (101 MHz, DMSO-d$_6$) δ170.6, 169.8, 135.3, 129.9, 128.3, 125.3, 58.0, 55.1, 24.6, 22.8, 22.3; HRMS (ESI): m/z calcd. for C$_{14}$H$_{20}$N$_3$O$_3$S$_2^+$[M]$^+$342.0941, found 342.0938.

((1-acetamido-1-carboxy-2-methylpropan-2-yl)disulfaneyl)((4-methoxyphenyl)amino) methaniminium chloride 4e:

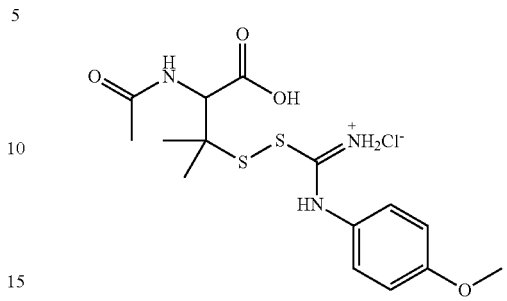

Light brown solid, mp=142-144° C., 368 mg, 58% yield, $^1$H NMR (400 MHz, DMSO-d$_6$) δ8.47 (d, J=9.1 Hz, 1H), 7.28 (d, J=9.0 Hz, 2H), 7.05 (d, J=9.0 Hz, 2H), 4.60 (d, J=9.1 Hz, 1H), 3.79 (s, 3H), 1.92 (s, 3H), 1.44 (s, 3H), 1.40 (s, 3H); $^{13}$C NMR (101 MHz, DMSO-d$_6$) δ170.6, 169.8, 167.1, 159.1, 127.7, 127.2, 115.1, 57.9, 55.5, 55.1, 24.5, 22.8, 22.3; HRMS (ESI): m/z calcd. for C$_{15}$H$_{22}$N$_3$O$_4$S$_2^+$[M]$^+$372.1046, found 372.1046.

((1-acetamido-1-carboxy-2-methylpropan-2-yl)disulfaneyl)((2-chlorophenyl)amino) methaniminium chloride 4f:

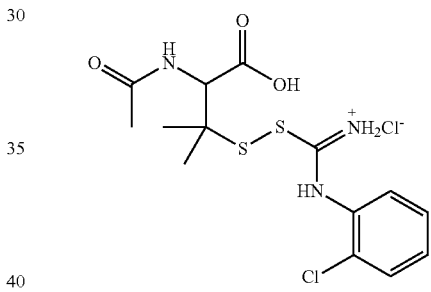

White solid, mp=152-154° C., 505 mg, 78% yield, $^1$H NMR (400 MHz, DMSO-d$_6$) δ8.50 (d, J=9.0 Hz, 1H), 7.63-7.38 (m, 4H), 4.57 (d, J=9.0 Hz, 1H), 1.92 (s, 3H), 1.45 (s, 3H), 1.42 (s, 3H); $^{13}$C NMR (101 MHz, DMSO-d$_6$) δ170.7, 169.8, 130.4, 128.6, 58.0, 54.9, 24.5, 22.9, 22.3; HRMS (ESI): m/z calcd. for C$_{14}$H$_{19}$ClN$_3$O$_3$S$_2^+$[M]$^+$ 376.0551, found 376.0547.

((1-acetamido-1-carboxy-2-methylpropan-2-yl)disulfaneyl)((4-chlorophenyl)amino) methaniminium chloride 4g:

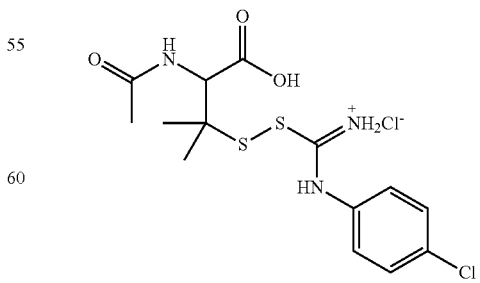

White solid, mp=143-145° C., 343 mg, 53% yield, $^1$H NMR (400 MHz, DMSO-d$_6$) δ8.43 (d, J=9.1 Hz, 1H), 7.51

(d, J=8.4 Hz, 2H), 7.34 (d, J=8.4 Hz, 2H), 4.59 (d, J=9.1 Hz, 1H), 1.91 (s, 3H), 1.42 (s, 3H), 1.39 (s, 3H); $^{13}$C NMR (101 MHz, DMSO-$d_6$) δ170.7, 169.7, 129.6, 126.4, 121.9, 57.9, 54.8, 24.6, 22.9, 22.3; HRMS (ESI): m/z calcd. for $C_{14}H_{19}ClN_3O_3S_2^+$[M]$^+$376.0551, found 376.0552.

((1-acetamido-1-carboxy-2-methylpropan-2-yl)disulfaneyl)((4-(trifluoromethyl)phenyl)amino)methaniminium chloride 4h:

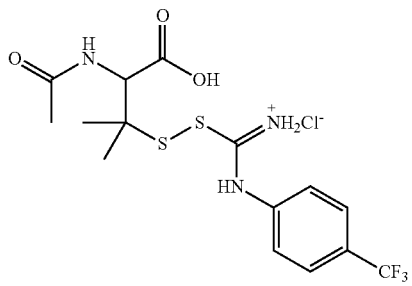

White solid, mp=151-153° C., 381 mg, 82% yield, $^1$H NMR (400 MHz, DMSO-$d_6$) 8.43 (d, J=9.2 Hz, 1H), 7.79 (d, J=8.5 Hz, 2H), 7.52 (d, J=8.5 Hz, 2H), 4.59 (d, J=9.2 Hz, 1H), 1.92 (s, 3H), 1.42 (s, 3H), 1.39 (s, 3H); $^{13}$C NMR (101 MHz, DMSO-$d_6$) δ170.7, 169.7, 126.7, 125.5, 124.5, 122.8, 57.8, 54.6, 24.6, 22.9, 22.3; HRMS (ESI): m/z calcd. for $C_{15}H_{19}F_3N_3O_3S_2^+$[M]$^+$410.0814, found 410.0813.

(t-butyldisulfaneyl)(phenylamino)methaniminium chloride 9:

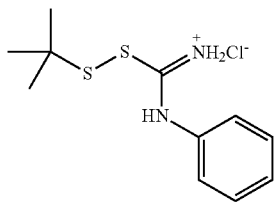

Colorless semisolid, 591 mg, 64% yield, $^1$H NMR (400 MHz, DMSO-$d_6$) δ7.53-7.51 (m, 2H), 7.43-7.34 (m, 3H), 1.38 (s, 9H); $^{13}$C NMR (101 MHz, DMSO-$d_6$) δ166.3, 135.9, 129.8, 127.9, 125.0, 50.9, 28.7; HRMS (ESI): m/z calcd. for $C_{11}H_{17}N_2S_2^+$[M]$^+$241.0828, found 241.0834.

Analysis of RSSH Trapping with N-ethylmaleimide Using UPLC-MS

RSSH trapping in the presence of N-ethylmaleimide (NEM) was carried out with a Waters Acquity/Xevo-G2 UPLC-MS system equipped with an ACQUITY UPLC BEH C18 column (2.1 mm×50 mm, 1.7 μm). Typically, RSSH precursor (1 eq) was incubated with NEM (5 to 20 eq) in freshly prepared pH 7 4 ammonium bicarbonate buffer (100 mM) containing DTPA (100 μM) at 37° C. An aliquot of the reaction mixture (300 μL) was withdrawn at specified time points, quenched with 0.25% formic acid (300 μL), and filtered through a 0.22 μm filter. The samples were then loaded into vials in an autosampler maintained at 4° C. and analyzed using UPLC-MS as follows: Mobile phase: 0-1 min 90% water+0% ACN+10% formic acid (0.1%); 1-7.5 min gradient up to 10% water+80% ACN+10% formic acid (0.1%); 7.5-8.4 min 10% water+80% ACN+10% formic acid (0.1%); 8.4-8.5 min gradient up to 90% water+0% ACN+10% formic acid (0.1%), 8.5-10 min 90% water+0% ACN+10% formic acid (0.1%). Flow rate=0.3 mL min$^{-1}$. The mass signals for products of RSSH trapping with NEM were obtained via deconvolution using MassLynx 4.1 software.

UPLC-MS Analysis of RSSH Generation from Precursor 1

To a solution of NEM (5 mM) in pH 7 4 ammonium bicarbonate (100 mM) with DTPA (100 μM) in a 20-mL scintillation vial, hydropersulfide precursor 1 (1 mM, total reaction volume 3 mL) was added. The resulting mixture was incubated at 37° C. for 30 min. An aliquot of 300 μL reaction mixture was withdrawn, quenched with 300 μL of formic acid (0.25%) and analyzed using UPLC-MS. The results of the analysis are shown in FIG. 5.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while various theories are presented describing possible mechanisms through with the compounds are effective, the compounds are effective regardless of the particular mechanism employed and the inventors are therefore not bound by theories described herein. The invention is not limited to the exact details shown and described, for variations obvious to one skilled in the art will be included within the invention defined by the claims.

What is claimed is:

1. A hydropersulfide precursor compound having the formula (I):

wherein $R^1$ is a $C_1$-$C_6$ alkyl group optionally substituted with one or more of a carboxylic acid, $C(O)OR^a$, $NHC(O)R^b$, $NHC(O)(CH_2)_2CH(NHC(O)R^c)(COOR^d)$, $NHC(O)(CH_2)_2CH(NH_2)(COOR^d)$, $C(O)NHCH_2COOR^e$, and a phenyl group optionally substituted with a lower alkyl, lower alkoxy, or trifluoromethyl moiety;

$R^2$ is a phenyl group that is optionally substituted with a halogen, methyl, methoxy, or trifluoromethyl moiety;

X is a halogen; and wherein $R^a$ is a $C_1$-$C_{20}$ alkyl moiety or a peptide chain comprising of 1-5 amino acids;

$R^b$ is a $C_1$-$C_{20}$ alkyl moiety;

$R^c$ is a $C_1$-$C_{20}$ alkyl moiety;

$R^d$ is H, a $C_1$-$C_{20}$ alkyl moiety, or a peptide chain comprising of 1-5 amino acids; and $R^e$ is H or a $C_1$-$C_{20}$ alkyl moiety.

2. The hydropersulfide precursor compound of claim 1, wherein $R^1$ is selected from the group consisting of

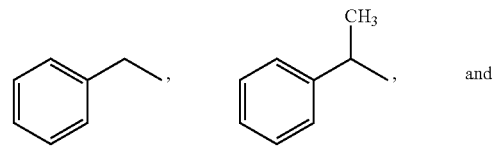

-continued

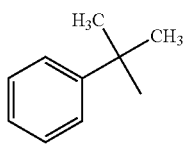

wherein the phenyl group may be unsubstituted or substituted with a lower alkyl, lower alkoxy, or trifluoromethyl moiety.

3. The hydropersulfide precursor compound of claim 1, wherein $R^1$ is a group having the formula (II):

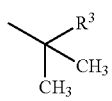

(II)

wherein $R^3$ is selected from methyl, ethyl, propyl,

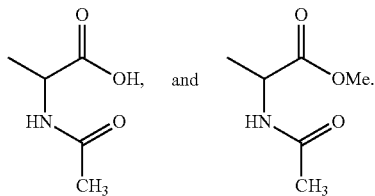

4. The hydropersulfide precursor compound of claim 1, wherein $R^1$ is

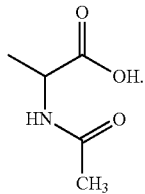

5. The hydropersulfide precursor compound of claim 1, wherein $R^1$ is

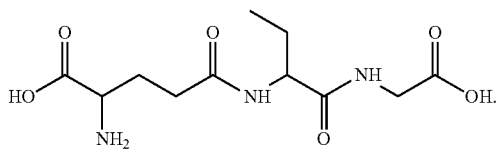 [SMILES: CCC(NC(=O)CCC(N)C(=O)O)C(=O)NCC(=O)O]

6. A process for preparing a hydropersulfide precursor compound of claim 1 comprising coupling an alkyl thiol compound having formula (III):

(III)

with an N-substituted thiourea compound having formula (IV):

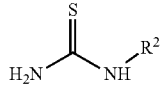

(IV)

under acidic conditions in the presence of hydrogen peroxide to form the hydropersulfide precursor compound having formula (I).

7. The process of claim 6, wherein $R^1$ is selected from the group consisting of

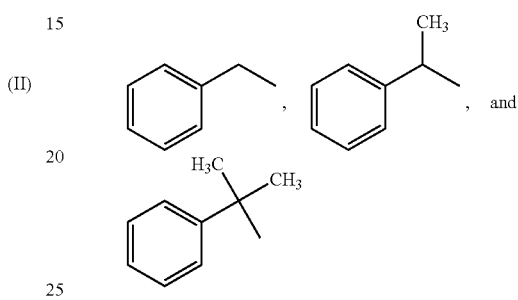

wherein the phenyl group may be unsubstituted or substituted with a lower alkyl, lower alkoxy, or trifluoromethyl moiety.

8. The process of claim 6, wherein $R^1$ is a group having the formula (II):

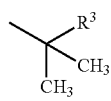

(II)

wherein $R^3$ is selected from methyl, ethyl, propyl,

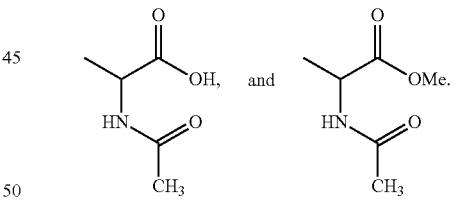

9. The process of claim 6, wherein $R^1$ is

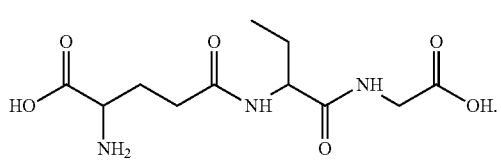 [SMILES: CCC(NC(=O)CCC(N)C(=O)O)C(=O)NCC(=O)O]

10. The process of claim 6, wherein an amount of hydrogen peroxide is present that is about equimolar with the concentration of the alkyl thiol.

11. The process of claim 6, wherein the coupling is carried out at a temperature of about 0° C.

12. A method of generating a hydropersulfide, comprising contacting a hydropersulfide precursor compound of claim 1 with an aqueous solution.

13. The method of claim 12, wherein $R^1$ is selected from the group consisting of

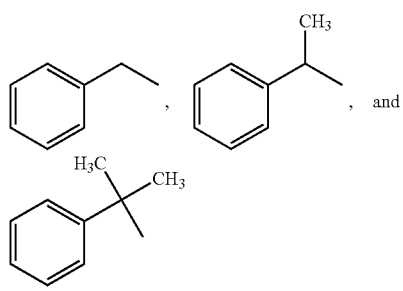

, and wherein the phenyl group may be unsubstituted or substituted with a lower alkyl, lower alkoxy, or trifluoromethyl moiety.

14. The method of claim 12, wherein $R^1$ is a group having the formula (II):

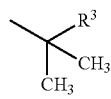

(II)

wherein $R^3$ is selected from methyl, ethyl, propyl,

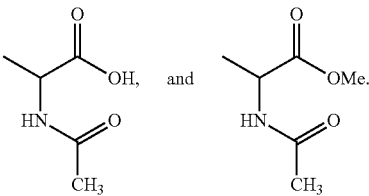

15. The method of claim 12, wherein $R^1$ is

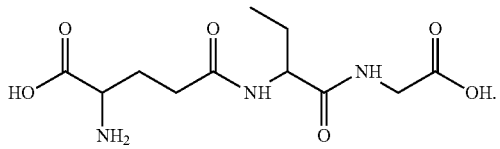 [SMILES: CCC(NC(=O)CCC(N)C(=O)O)C(=O)NCC(=O)O]

16. The method of claim 12, wherein the hydropersulfide is generated in vivo.

17. The method of claim 12, wherein the hydropersulfide is generated in a therapeutically effective amount in a subject in need of smooth muscle relaxation, inhibition of inflammation, or cardioprotection.

* * * * *